(12) United States Patent
Callol

(10) Patent No.: US 6,464,723 B1
(45) Date of Patent: Oct. 15, 2002

(54) RADIOPAQUE STENTS

(75) Inventor: Joseph R. Callol, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/298,263

(22) Filed: Apr. 22, 1999

(51) Int. Cl.$^7$ .................................................. A61F 2/06

(52) U.S. Cl. ...................... 623/1.34; 623/1.16; 606/153; 606/194

(58) Field of Search .............................. 623/1.16, 1.34, 623/1.15; 606/153, 191, 198, 192, 194, 195

(56) References Cited

U.S. PATENT DOCUMENTS

| | | |
|---|---|---|
| 3,288,728 A | 11/1966 | Gorham |
| 3,839,743 A | 10/1974 | Schwarcz |
| 4,086,916 A | 5/1978 | Freeman et al. |

(List continued on next page.)

FOREIGN PATENT DOCUMENTS

| | | |
|---|---|---|
| DE | A-44 07 079 | 9/1994 |
| DE | 296 07 916 | 8/1996 |
| EP | 0 380 668 A1 | 4/1989 |
| EP | 0 448 016 A | 9/1991 |
| EP | 0 517 075 A1 | 12/1992 |
| EP | 0 540 290 A2 | 5/1993 |
| EP | 0 565 251 A1 | 10/1993 |
| EP | 0 604 022 | 1/1994 |
| EP | 0 578 998 | 6/1994 |
| EP | A 0 621 017 | 10/1994 |
| EP | 0 679 372 A | 11/1995 |
| EP | 0 679 373 A | 11/1995 |
| EP | 0 709 068 | 5/1996 |
| EP | 0 847 733 | 6/1998 |
| FR | 2677872 A1 | 12/1992 |
| WO | WO 91/17789 | 11/1991 |
| WO | WO 93/06792 | 4/1993 |
| WO | WO 95/03010 | 2/1995 |
| WO | WO 95/29647 | 11/1995 |
| WO | WO 96/24393 | 8/1996 |
| WO | WO 99/15107 | 4/1999 |

OTHER PUBLICATIONS

Application for U.S. Letters patent Ser. No. 08/233,046 filed Apr. 25, 1994.
Application for U.S. Letters patent Ser. No. 08/564,936 (FWC of 08/233,046) filed Nov. 29, 1995.
Application for U.S. Letters patent Ser. No. 08/234,547 filed Apr. 28, 1994.
Application for U.S. Letters patent Ser. No. 08/559,331 (FWC of 08/234,547) filed Nov. 17, 1995.
Union Carbide Technology Letter, New Business Department—Parylene, Oct. 1973, No. 7 (8 pages).
Union Carbide, Electronic Materials, Parylene Products, Oct. 1973, No. 9 (23 pages).
Union Carbide Technology Letter, May 1974, No. 11 (12 pages).
Union Carbide Technology Letter, Oct. 1975, No. 15 (13 pages).

(List continued on next page.)

Primary Examiner—David J. Isabella
Assistant Examiner—Urmi Chattopadhyay
(74) Attorney, Agent, or Firm—Fulwider Patton Lee & Utecht, LLP

(57) ABSTRACT

A stent is formed from a series of linked, radially aligned expandable rings. The end rings are formed of a radiopaque material while the rings positioned between the end rings are formed of a radio-transparent material. Two very bright fluoroscopic images are created by the end rings, without any compromise in the strength of the stent, while the center of the stent remains transparent so as not to obscure the image of lesion area when the stent is being centered therein.

13 Claims, 2 Drawing Sheets

U.S. PATENT DOCUMENTS

| | | | |
|---|---|---|---|
| 4,346,028 A | 8/1982 | Griffith | |
| 4,633,873 A | 1/1987 | Dumican et al. | |
| 4,656,083 A | 4/1987 | Hoffman et al. | |
| 4,681,110 A | 7/1987 | Wiktor | |
| 4,699,611 A | 10/1987 | Bowden | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallsten et al. | |
| 4,733,665 A | 3/1988 | Palmaz | |
| 4,739,762 A | 4/1988 | Palmaz | |
| 4,768,507 A | 9/1988 | Fischell et al. | |
| 4,776,337 A | 10/1988 | Palmaz | |
| 4,816,339 A | 3/1989 | Tu et al. | |
| 4,830,003 A | 5/1989 | Wolff et al. | |
| 4,856,516 A | 8/1989 | Hillstead | |
| 4,877,030 A | 10/1989 | Beck et al. | |
| 4,878,906 A | 11/1989 | Lindemann et al. | |
| 4,879,135 A | 11/1989 | Greco et al. | |
| 4,886,062 A | 12/1989 | Wiktor | |
| 4,913,141 A | 4/1990 | Hillstead | |
| 4,943,346 A | 7/1990 | Mattelin | |
| 4,994,071 A | 2/1991 | MacGregor | |
| 4,994,298 A | 2/1991 | Yasuda | |
| 5,019,090 A | 5/1991 | Pinchuk | |
| 5,047,050 A | 9/1991 | Apresani | |
| 5,053,048 A | 10/1991 | Pinchuk | |
| 5,059,211 A | 10/1991 | Stack et al. | |
| 5,062,829 A | 11/1991 | Pryor et al. | |
| 5,067,491 A | 11/1991 | Taylor, II et al. | |
| 5,084,065 A | 1/1992 | Weldon et al. | |
| 5,085,629 A | 2/1992 | Goldberg et al. | |
| 5,102,417 A | 4/1992 | Palmaz | |
| 5,104,404 A | 4/1992 | Wolff | |
| 5,108,755 A | 4/1992 | Daniels et al. | |
| 5,116,365 A | 5/1992 | Hillstead | |
| 5,123,917 A | 6/1992 | Lee | |
| 5,133,732 A | 7/1992 | Wiktor | |
| 5,135,536 A | 8/1992 | Hillstead | |
| 5,156,623 A | 10/1992 | Hakamatsuka et al. | |
| 5,163,951 A | 11/1992 | Pinchuk et al. | |
| 5,163,952 A | 11/1992 | Froix | |
| 5,163,958 A | 11/1992 | Pinchuk | |
| 5,192,311 A | 3/1993 | King et al. | |
| 5,197,977 A | 3/1993 | Hoffman, Jr. et al. | |
| 5,222,971 A | 6/1993 | Willard et al. | |
| 5,226,913 A | 7/1993 | Pinchuk | |
| 5,234,456 A | 8/1993 | Silvestrini | |
| 5,234,457 A | 8/1993 | Andersen | |
| 5,236,447 A | 8/1993 | Kubo et al. | |
| 5,269,802 A | 12/1993 | Garber | |
| 5,282,823 A | 2/1994 | Schwartz et al. | |
| 5,282,860 A | 2/1994 | Matsuno et al. | |
| 5,289,831 A | 3/1994 | Bosley | |
| 5,290,271 A | 3/1994 | Jernberg | |
| 5,304,200 A | 4/1994 | Spaulding | |
| 5,306,286 A | 4/1994 | Stack et al. | |
| 5,314,444 A | 5/1994 | Gianturco | |
| 5,314,472 A | 5/1994 | Fontaine | |
| 5,330,500 A | 7/1994 | Song | |
| 5,342,348 A | 8/1994 | Kaplan | |
| 5,342,621 A | 8/1994 | Eury | |
| 5,356,433 A | 10/1994 | Rowland et al. | |
| 5,360,443 A | 11/1994 | Barone et al. | |
| 5,364,354 A | 11/1994 | Walker et al. | |
| 5,383,927 A | 1/1995 | De Gioicoechea et al. | |
| 5,389,106 A | 2/1995 | Tower | |
| 5,423,849 A | 6/1995 | Engelson et al. | |
| 5,423,885 A | 6/1995 | Williams | |
| 5,514,154 A | 5/1996 | Lau et al. | |
| 5,562,728 A | 10/1996 | Lazarus | |
| 5,599,301 A | 2/1997 | Jacobs et al. | |
| 5,609,629 A | 3/1997 | Fearnot et al. | |
| 5,628,787 A | 5/1997 | Mayer | |
| 5,637,113 A | 6/1997 | Tartaglia et al. | |
| 5,649,951 A | 7/1997 | Davidson | |
| 5,674,242 A | 10/1997 | Phan et al. | |
| 5,741,327 A | * 4/1998 | Frantzen | 623/1.34 |
| 5,827,321 A | * 10/1998 | Roubin et al. | 606/195 |
| 5,858,556 A | 1/1999 | Eckert et al. | |
| 5,907,893 A | * 6/1999 | Zadno-Azizi et al. | |
| 5,948,016 A | * 9/1999 | Jan | 623/1.16 |

OTHER PUBLICATIONS

Union Carbide, Electronic Materials, Parylene Products, Mar. 1976, No. 16 (4 pages).

Eskin, et al., *Growth of Cultured Calf Aortic Smooth Muscle Cells on Cardiovascular Prosthetic Materials*, J. Biomed. Mater. Res., vol. 10, pp. 113–122 (1976).

Loeb, et al., *Parylene as a Chronically Stable, Reproducible Microelectrode Insulator*, IEEE Transactions on Biomedical Engineering, Mar. 1977 (pp. 121–128).

Union Carbide, Electronic Materials, Parylene Products, Aug. 1977, No. 18 (7 pages).

Union Carbide, Electronic Materials, Parylene Products, Oct. 1977, No. 1 Revision 2 (7 pages).

Union Carbide, Electronic Materials, Parylene Products, Oct. 1977 No. 2 Revision 1 (9 pages).

Union Carbide, Electronic Materials, Parylene Products, Oct. 1977 No. 3 (21 pages).

Union Carbide, Electronic Materials, Parylene Products, Oct. 1977 No. 4 (13 pages).

Union Carbide, Electronic Materials, Parylene Products, Oct. 1977 No. 6 (12 pages).

Union Carbide, Electronic Materials, Parylene Products Oct. 1977 No. 7 Revision 1 (8 pages).

Union Carbide, Electronic Materials, Parylene Products, Oct. 1977 No. 8 Edited (19 pages).

Union Carbide, Electronic Materials, Parylene Products, Oct. 1977 No. 10 (50 pages).

Union Carbide, Electronic Materials, Parylene Products, Oct. 1977 No. 11 (12 pages).

Union Carbide, Electronic Materials, Parylene Products, Oct. 1977 No. 12, Revision 1 (6 pages).

Union Carbide, Electronic Materials, Parylene Products, Oct. 1977 No. 13, Revision 1 (7 pages).

Union Carbide, Electronic Materials, Parylene Products, Oct. 1977 No. 14. Revision 1 (11 pages).

Union Carbide, Electronic Materials, Parylene Products, Oct. 1977 No. 15, Revision 1 (8 pages).

Union Carbide, Electronic Materials, Parylene Products, Oct. 1977 No. 17, Revision 1 (11 pages).

*ISEEE Transactions on Biomedical Engineering*, vol. BME–27, No. 11, Nov. 1980 (5 pages).

Sadhir, et al., *The Adhesion of Glow–Discharge Polymers, Silastic and Parylene to Implantable Platinum Electrodes: Results of Tensile Pull Tests After Exposure to Isotonic Sodium Chloride*, 10/81, vol. 2, Biomaterials (pp. 239–243).

Hahn, et al., *Glow Discharge Polymers as Coatings for Implanted Devices*, John M. Dalton Research Center, University of Missouri–Columbia and the Graduate Center for Materials Research, 1981 (pp. 109–113).

Union Carbide, Electrode Materials, Parylene Products, Jan. 18, 1982, No. 5, Revision 4 (17 pages).

Hahn, et al., Biocompatibility of Glow–Discharge–Polymerized Films and Vacuum–Deposited Parylene, *Journal of Applied Polymer Science: Applied Polymer Symposium* 38, 55–64 (1984).

Casper, et al., Fiber–Reinforced Absorbable Composite for Orthopedic Surgery, *Polymeric Materials Science and Engineering*, Proceedings of ACS Division of Polymeric Materials: Science & Engineering, vol. 53, Fall Mtg. 1985.

Kelley, et al., Totally Resorbable High–Strength Composite Material, *Advances in Biomedical Polymers*, Edited by Charles G. Gebelein (1987).

Yuen, et al., Tissue Response to Potential Neuroprosthetic Materials Implanted Subdurally, Biomaterials, Mar. 1987, vol. 8 (pp. 57–62).

Nichols, et al., Electrical Insulation of Implantable Device by Composite Polymer Coatings, Dalton Research Center, University of Missouri, 1987.

Schmidt, et al., long–Term Implants of Parylene–C Coated Microelectrodes, Medical & Biological Engineering & Computing, Jan. 1988 (pp. 96–101).

Olson, Parylene, a Biostable Coating for Medical Applications, for Nova Tran Parylene Coating Services (Jul. 25, 1988; Nov. 14, 1988).

Beach, et al., Xylylene Polymers, *Encyclopedia of Polymer Science and Engineering*, vol. 17, Second Edition, pp. 990–1025, 1989.

Muller, et al., Advances in Coronary Angioplasty: Endovascular Stents, *Coronary Artery Disease*, Jul./Aug. 1990, vol. 1, No. 4.

Loh et al., *Plasma Enhanced Parylene Deposition*, Antec, pp. 1099–11033, 1991.

Wong, M.D., et al., An Update on Coronary Stents, *Cardio*, Feb. 1992.

Gebelein, et al., *Biomedical and Dental Applications of Polymers*, Polymer Science and Technology, vol. 14 (no date) (pp. 143–161).

The Parylene Press(A Publication of Specialty Coating Systems, Inc.) Winter 1992 (7 pages).

Charlson, et al., *Temperature Selective Deposition of Parylene–C*, IEEE Transactions on Biomedical Engineering, vol. 39, No. 2, Feb. 1992 (pp. 202–206).

Bull: *Parylene Coating for Medical Applications*, Medical Product Manufacturing News, Mar. 1993 (2 pages).

*The Parylene Press* (A Publication of Specialty Coating Systems, Inc.), Spring 1993 (6 pages).

*The Parylene Press* (A Publication of Specialty Coating Systems, Inc.), Summer 1993 (4 pages).

*Information Regarding Parylene–C Coating for ACS Metal Stent*, In–House Memorandum from Ed Newton to Joe Callol, et al., Oct. 15, 1993 attaching Parylene, A biostable Coating for Medical Applications by Roger Olson Moody: *Vacuum Coating Ultrasonic Transducers*, Sensors, Dec. 1993 (1 page).

*Union Carbide A–174 Silane*, Sales Brochure, Union Carbide Adhesion Promoters, Jan. 1968 (5 pages).

*Parylene Conformal Coatings Specifications and Properties*, Sales Brochure, Union Carbide Specialty Coating Systems (12 pages).

*Parylene Environmentally Compatible Conformal Coatings for Electronic Components Assemblies and Precision Parts*, Brochure, Union Carbide Electronics Division (14 pages).

*Parylene and Nova Tran® Parylene Coating Services for Unmatched Conformal Coating Performance*, Brochure, Union Carbide Specialty Coating Systems (21 pages).

*Repair and Recoating of Parylene Coated Printed Circuit Boards*, Brochure, Union Carbide Specialty Coating Systems (15 pages).

*Nova Tran® Custom Coating Services, Parylene Conformal Coating*, Brochure, Union Carbide (8 pages).

*Parylene, a Biostable Coating for Medical Applications* Brochure, Union Carbide Specialty Coating Systems (6 pages).

*Typical Parylene Properties,* Priintout, Pata Tech Coating Company; *Lab Top$^{200}$ Parylene Depostition System Model 3000,* Sales Brochure, Para Tech Coating Company (7 pages).

* cited by examiner

RADIOPAQUE STENTS

BACKGROUND OF THE INVENTION

This invention generally relates to endoprosthesis devices, most often referred to as stents, and more particularly pertains to the radiopaque marking of such devices.

Stents are useful in the treatment of atherosclerotic stenosis in blood vessels and are generally tubular shaped devices which function to hold open a segment of a blood vessel or other anatomical lumen. They are particularly suitable for use in supporting and holding back a dissected arterial lining which could otherwise occlude the fluid passageway therethrough.

In order to accomplish precise placement of stents, various means are employed to identify the position of the stent within a blood vessel. One means frequently described for accomplishing precise placement of a stent is the attachment of radiopaque markers to the stent so that through the use of fluoroscopy, the position of the stent within a blood vessel can be identified. Once the stent with its radiopaque markers has been implanted, subsequent checkups of the treated segment are easily performed since the markers remain visible under fluoroscopic illumination.

Conventional radiopaque markers, however, have a number of limitations. Upon attachment to a stent, conventional radiopaque markers may project from the surface of the stent, thereby comprising a departure from the ideal profile of the stent. Such conventional radiopaque markers protrude from the walls of the stent and depending upon their location upon the stent, may either project inwardly to disrupt blood flow or outwardly to traumatize the walls of the blood vessel. In addition, conventional radiopaque markers have the disadvantage in that their attachment to the stent can be tedious and imprecise. Moreover, the configuration of many heretofore known markers fails to provide a precise indication of the location and position of the stent. Finally, the galvanic corrosion that might result from the contact of two disparate metals, i.e., the metal used in the construction of the stent and the radiopaque metal of the marker could eventually cause the marker to become separated from the stent which could be problematic should the marker embolize downstream and occlude the artery.

Other conventional radiopaque markers restrict the expansion capabilities of an expandable stent by adding rigidity to the stent in areas designated for stent deformation. Still other conventional stents utilize material, such as tantalum, that is effective for use in identifying the location of a stent within a vessel, but fluoroscopically illuminates so brightly so as to obscure proper visibility of the arterial lesion, thereby impairing the ability to repair the lesion. Finally, conventional radiopaque markers do not generally, under fluoroscopy, provide the operator with means to accurately access stent length and diameter.

Stents have also been previously marked by plating selected portions thereof with a radiopaque material. An advantageously selected pattern of plated areas would theoretically allow the position, length and diameter of the stent to be discerned. However, due to the minimal thickness of the plating, only an extremely faint fluoroscopic image can be generated which may ultimately limit its utility.

To overcome the problems and limitations associated with stents having conventional radiopaque markers, or plated markings, it would be desirable to employ radiopaque markers or markings that do not limit the expansion capabilities of an expandable stent, nor alter the profile of the stent, that are clearly visible, that provide means to assess stent length and diameter, that do not obscure the blood vessel lesion being repaired and that are not detrimentally affected by galvanic corrosion.

SUMMARY OF THE INVENTION

The present invention provides for the radiopaque marking of a stent that effectively identifies the position, diameter and length of a stent both while fitted to the delivery device as well as upon implantation within a blood vessel, yet does not obscure the lesion being repaired. The marking is an integral part of a stent, does not protrude from the surface of the stent and does limit the expansion capabilities of the stent. Furthermore, the marking is not adversely affected by galvanic corrosion. The radiopaque marking of the present invention may be adapted to stents having various geometric shapes and that are constructed of any of various materials.

In a preferred embodiment, the stent of the present invention is of wire construction wherein a plurality of shaped wire rings are axially aligned and appropriately linked. This type of stent is well known in the art and offers significant advantages in terms of expandability, radial strength, longitudinal flexibility, and longitudinal stability during expansion. However, no radiopaque materials are known that satisfy the strength and biocompatibility requirements of such application. In order to render such stents fluoroscopically visible in accordance with the present invention, the proximal most and distal most rings are wholly formed of a radiopaque material.

Such construction provides all of the advantages set forth above. Positioning of the radiopaque material at the extreme ends of the stent renders the position of the stent clearly and precisely ascertainable without interfering with the visibility of a lesion therebetween. Because the end rings are wholly constructed of radiopaque material, they create a brilliant image when fluoroscopically illuminated, unequivocally revealing the position of the stent. Additionally, because the structure of the two end rings is substantially identical to the structure of the stent's other rings, all of the rings, including the end rings expand at the same rate during deployment of the stent. This causes the marker rings to engage the vessel walls in the same manner as the stent's other rings and thus become firmly embedded therein. Should the end rings eventually become separated from the balance of the stent, there is no danger of them being carried downstream or otherwise create an obstruction due to their expanded configuration and growth of an internal layer over the stent. Additionally, because the end rings are of the same size and shape as the rings in the body of the stent, the radiopaque marking of the stent does not pose an impediment to the flow of blood thereover and is less likely therefore to lead to platelet activation and thrombosis formation. Similarly, there is no likelihood of the marker impinging into the vessel walls to an inordinate degree and cause trauma.

The stent may be constructed using any of a variety of techniques including fabricating the non-radiopaque series of linked rings and the radiopaque end rings separately and then subsequently joining them such as by laser welding. Alternatively, a tube may be constructed wherein a flat section of radio-transparent material is first joined to two flat strips of radiopaque material afterwhich the joined material is formed into a cylinder. Fabrication of the stent may be accomplished in the conventional manner by then laser cutting or etching the cylinder to define an expandable configuration of struts.

These and other features and advantages of the present invention will become apparent from the following detailed description of a preferred embodiments which, taken in conjunction with the accompanying drawings, illustrate by way of example the principles of the invention.

DETAILED DESCRIPTION OF PREFERRED EMBODIMENTS

The stent of the present invention includes radiopaque markings that render its position clearly visible without obscuring the image of the treatment site. This enables the position of the stent to be monitored as it is being advanced through the vasculature by the delivery catheter, it allows the stent to be very precisely positioned relative the target site, allows its deployment to be verified and its continued presence to be detected at any time thereafter.

Figure 1:
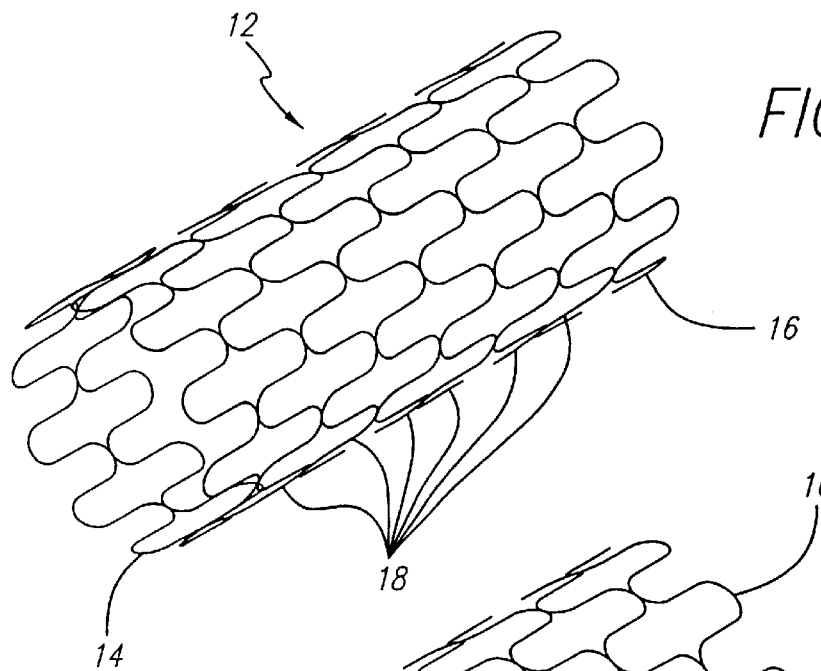
FIG. 1 is a perspective view of a stent of the present invention.

FIG. 1 illustrates a preferred embodiment representative of the present invention. The stent 12 is of wire or tubular construction wherein a series of rings having a serpentine or undulating pattern are axially aligned and joined to one another. The undulating configuration allows the rings to be radially expanded such that the stent device can be introduced into the vasculature and advanced therethrough while in a relatively small diameter, low profile state and then expanded into a relatively large diameter, deployed state to provide support to the lumen. Expansion can be achieved by, for example, the inflation of an expandable balloon about which the stent is carried as it is advanced into place.

As is shown in FIG. 1, the end rings 14,16 may have the same physical configuration as the rings 18 of the center section but nonetheless are differentiated in that they are constructed of a material that is different than the material used in the construction of the balance of the stent. More particularly, while the rings 18 of the central section are constructed of a radio-transparent material such as stainless steel, nickle titanium (Nitinol) or titanium, the end rings 14,16, are constructed of a highly radiopaque material such as tantalum, platinum-iridium, platinum or gold. Rings 18 may be formed from a tube using laser cutting techniques, chemical etching, or electro discharge machinery (EDM) and end rings 14,16 made separately and attached to rings 18 by known means such as laser welding. The stent pattern also can be formed by laser cutting a flat sheet and rolling the pattern into a cylinder and joining the longitudinal edges by laser welds or by obtaining tubes of each type of material and welding them together in their tubular configuration. Alternatively, the rings may all be fabricated separately and then attached to one another by any of various well known means such as by welding, laser welding, resistance welding, diffusion bonding, mechanical means or with the use of adhesives. Laser cutting and chemical etching processes are disclosed in U.S. Pat. Nos. 5,421,955 and 5,759,192, which are incorporated herein by reference thereto.

Figure 2:
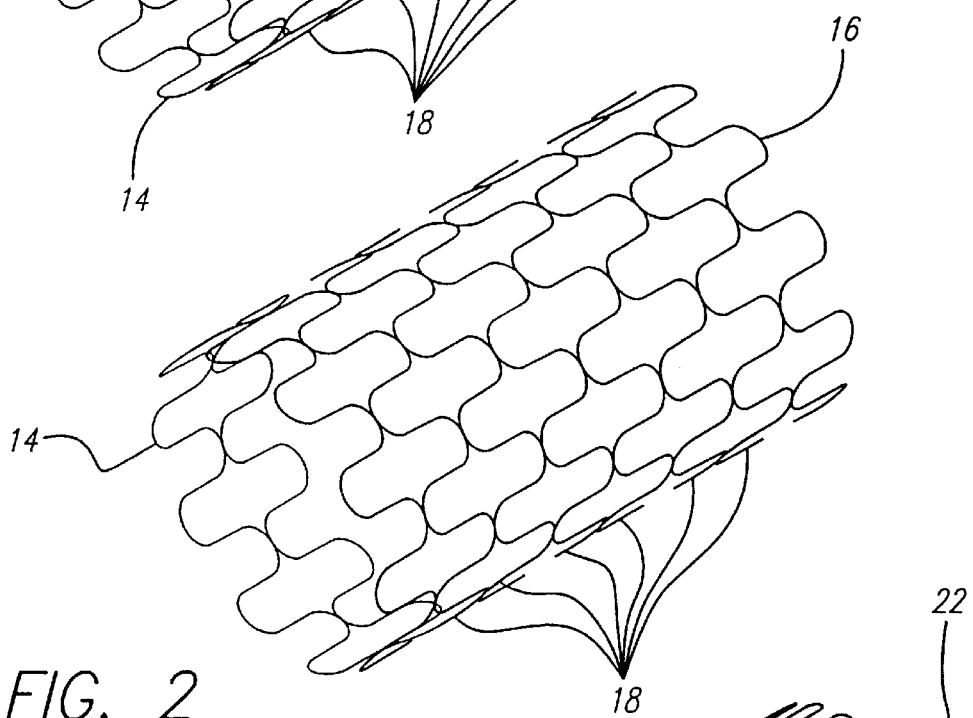
FIG. 2 is a perspective of the stent shown in FIG. 1 in its expanded state.
Figure 3:
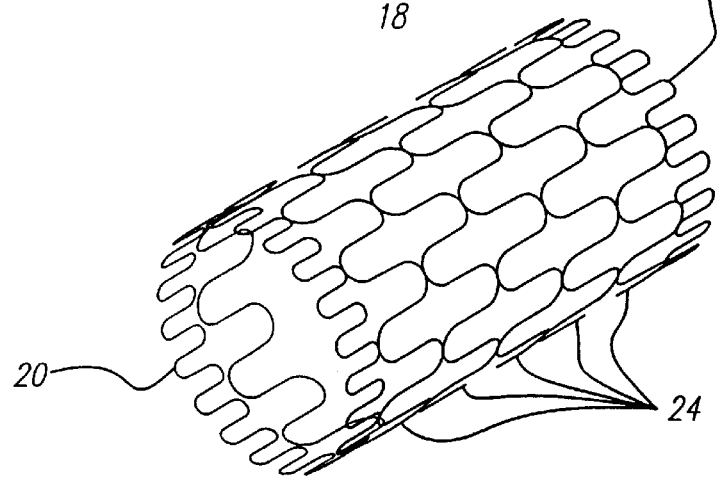
FIG. 3 is a perspective view of an alternative embodiment stent of the present invention.

FIG. 2 illustrates the stent shown in FIG. 1 in its expanded state. The radiopaque rings 14,16, undergo deformation in the same uniform manner and to substantially the same extent as the central structural rings 18. The end rings may be configured and sized to be functional such that they participate in supporting the vessel wall upon expansion. Alternatively, they may be wholly non-functional in terms of their ability to provide support. In such case, their configuration must be selected merely so as not to interfere in the primary functions of the stent and not interfere with blood flow. FIG. 3 illustrates an alternative embodiment wherein the configuration of the end rings 20,22 is different than the configuration of the rings 24 in the stent's central section.

While FIGS. 1–3 depict a single radiopaque ring at each end of the stent, more than one ring at the ends of the stent can be formed of radiopaque material to further enhance the visibility of the stent.

The material used in the construction of all but the end rings is selected for its structural characteristics such as radial strength, expansion capability, longitudinal flexibility as well as its biocompatibility. In addition, so as not to obstruct the image of a lesion to be treated, such material must also be substantially radio-transparent. In contrast, the material used in the construction of the end rings is selected for its radiopacity and biocompatibility.

Figure 4:
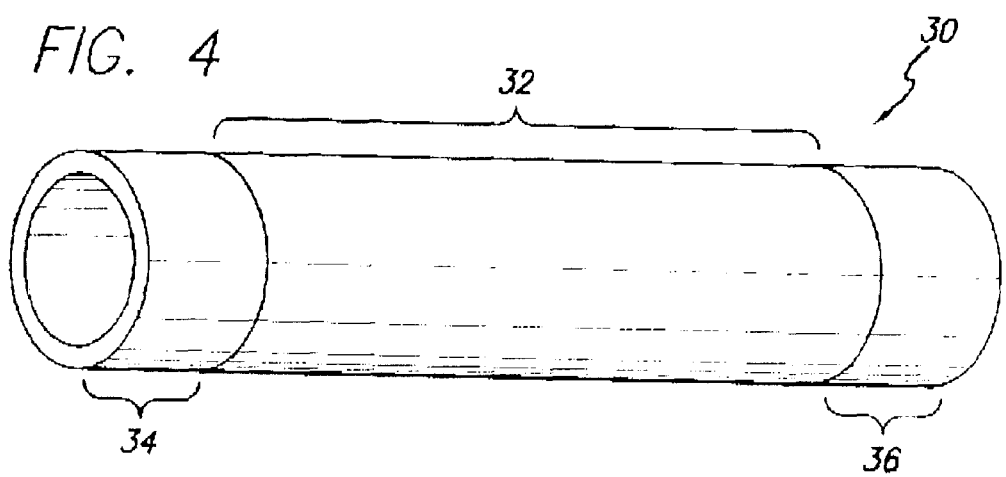
FIG. 4 is a perspective view showing a distal and proximal end tube attached to a center tube.
Figure 5:
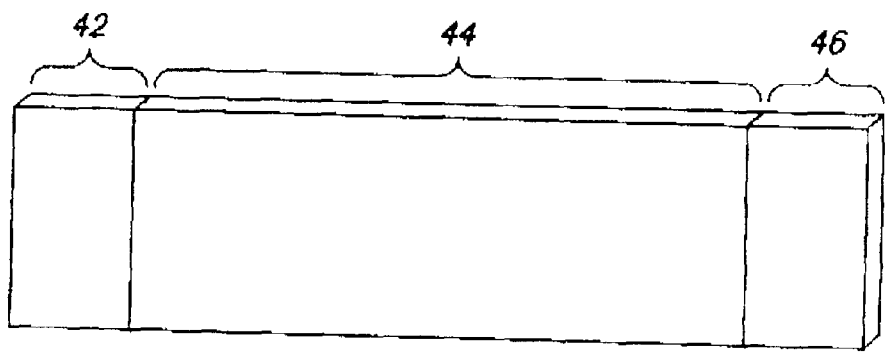
FIG. 5 is a perspective view showing distal and proximal end sheet attached to a center sheet to form a planar body.
Figure 6:
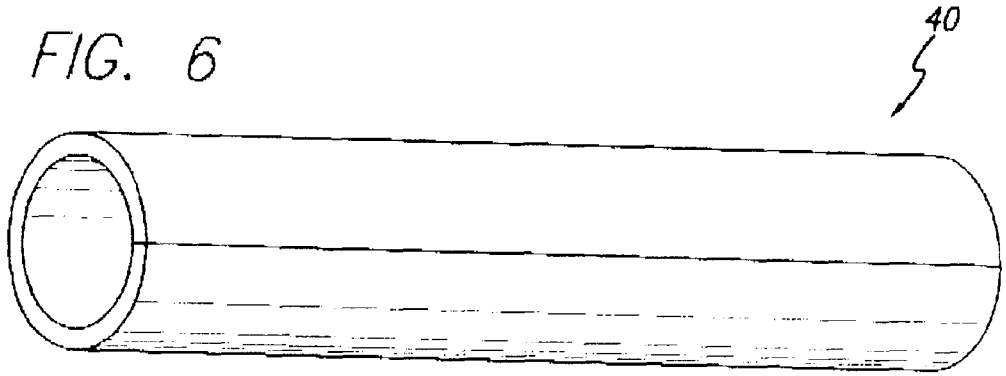
FIG. 6 is a perspective view showing the planar body of FIG. 5 rolled about a longitudinal axis to form a tubular body.

As shown in FIG. 4, the stent is constructed from a cylinder 30 having a center section 32 of a structural material such as Nitinol or stainless steel while its proximal and distal ends 34, 46 are formed of radiopaque material. Alternatively, sheets 42, 44, and 46 of the two different materials may be attached to one another by any of many well known means after which the cylinder 40 is formed (FIGS. 5 and 6). In order to impart the necessary flexibility and expandability to the cylinder, voids are then either etched therein or cut therein by a laser. Advantageous orientation and shaping of such voids, as is well known in the art, serves to define the stent struts. The ability of the struts to deform and become reoriented allows the stent to undergo radial expansion. The sections of radiopaque material at the ends of the stent impart the desired visibility to the stent without interfering in its deployment.

In use, the stent is first fitted about the expandable balloon element of a balloon catheter and tightly crimped thereon. In such state, the position of the stent relative to the delivery device is visible as fluoroscopic illumination causes the end rings or end sections of the stent as well as radiopaque markers positioned on the delivery device to be clearly visible. Their relative positions serve to indicate the position of the stent on the delivery device.

As the stent carrying delivery catheter is inserted into and advanced through the vasculature, the position of the stent relative the delivery device can be continually monitored fluoroscopically. Any shifting of the stent relative to the catheter can be immediately spotted and the appropriate remedial action taken. The radiopacity of the ends of the stent also enhances the visibility of the stent/delivery catheter combination to enable its progress through the vasculature to be followed.

As the deployment site is approached, the position of the stent is fine tuned by centering its two illuminated end rings within the now dilated lesion area. While the use of highly radiopaque material in the construction of the end rings causes the end rings to illuminate very brightly, their positioning at the extreme ends of the stent ensures that their images do not obscure the substantially fainter image of the dilated lesion when positioned therein. The stent can therefore be precisely centered within the lesion.

The radiopaque end rings of the stent also allow its expansion to be monitored as an increase in radius causes the profile of each of the rings to appear longer and somewhat narrower. Failure of the balloon to inflate or to inflate uniformly is detectable by a close inspection of the image of the rings. No change in the images of the two rings indicates a failure to expand, while a disparity in the two images suggests non-uniform expansion.

The fact that a stent has been implanted is readily evident during a radiological examination of the patient later in time as the bright images generated by the radiopaque elements can not be over looked. Additionally, because the radiopaque components are expanded against the vessel walls, they remain in place even if one or both end rings becomes separated from the rest of the stent. As a result, the position of the stent continues to be clearly discernable and the possibility of an end ring from migrating is effectively obviated.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. An intravascular stent having a generally cylindrical shape and having a distal end and a proximal end, comprising:
    a plurality of ring elements of uniform configuration and dimension aligned along a longitudinal axis wherein linkages of uniform configuration and dimension link all adjacent ring elements and wherein ring elements near said distal end and ring elements near said proximal end are formed of radiopaque material while all other ring elements are formed of radiotransparent material.

2. The stent of claim 1, wherein said radio-transparent material is selected from the group comprising stainless steel, nickel-titanium, and plastic and said radiopaque material is selected from the group comprising tantalum, iridium-platinum, platinum and gold.

3. The stent of claim 1, wherein each of said ring elements comprise wire structures.

4. The stent of claim 1, wherein said ring elements are defined by voids formed in a tubular structure.

5. The stent of claim 1, wherein each of said ring elements are formed from a tubular member.

6. The stent of claim 1, wherein said ring elements are formed from a flat sheet of material.

7. A method of making an intravascular stent, including:
    selecting an elongated center tube having two opposing ends and formed of radio-transparent material, a distal end tube formed of radiopaque material, and a proximal end tube formed of radiopaque material;
    joining said distal end tube to one of said opposing ends, and said proximal end tube to the other of said opposing ends, whereby said tubes are aligned along a common longitudinal axis and cooperate to form a unitary cylindrical body;
    cutting a predetermined, uniform stent pattern having a plurality of interconnected cylindrical ring elements on said cylindrical body to form said intravascular stent, said stent being unitarily constructed and having a radio-transparent center section, a radiopaque distal end section, and a radiopaque proximal end section.

8. The method of claim 7, wherein said joining step includes welding said tubes together.

9. The method of claim 7, wherein said joining step includes bonding said tubes together.

10. The method of claim 7, wherein at least one of said tubes is constructed from a flat sheet rolled about a longitudinal axis.

11. A method of making an intravascular stent, including:
    providing an elongated center sheet having a first end and a second end and formed of radio-transparent material, a distal end sheet formed of radiopaque material, and a proximal end sheet formed of radiopaque material;
    joining said distal end sheet to said first end and joining said proximal end sheet to said second end to form an elongated unitary planar body;
    rolling said planar body about a longitudinal axis to form a hollow cylinder; and
    cutting a predetermined stent pattern having a plurality of interconnected cylindrical ring elements on said cylinder to form said intravascular stent, said stent being unitarily constructed and having a radio-transparent center section, a radiopaque distal end section, and a radiopaque proximal end section.

12. The method of claim 11, wherein said joining step includes welding said sheets together.

13. The method of claim 12, wherein said joining step includes bonding said sheets together.

* * * * *

UNITED STATES PATENT AND TRADEMARK OFFICE
CERTIFICATE OF CORRECTION

PATENT NO.    : 6,464,723 B1
DATED         : October 15, 2002
INVENTOR(S)   : Joseph R. Callol It is certified that error appears in the above-identified patent and that said Letters Patent is hereby corrected as shown below:

Title page,
Item [56], References Cited, OTHER PUBLICATIONS, at the "*Information Regarding Parylene-C...*" reference, after "Olson" delete "Moody:" and add a period -- . --; and before "*Vacuum*", add -- Moody: --.

Column 6,
Line 45, change "12", to read -- 11 --.

Signed and Sealed this

Twenty-fifth Day of March, 2003

JAMES E. ROGAN
*Director of the United States Patent and Trademark Office*